United States Patent [19]

Lennon et al.

[11] Patent Number: 4,963,325

[45] Date of Patent: Oct. 16, 1990

[54] SWAB EXPRESSOR IMMUNOASSAY DEVICE

[75] Inventors: Donald J. Lennon, Hopedale; Paul B. Foster, Quincy, both of Mass.

[73] Assignee: Hygeia Sciences, Inc., Newton, Mass.

[21] Appl. No.: 191,158

[22] Filed: May 6, 1988

[51] Int. Cl.$^5$ ............................ G01N 1/00; B01L 3/00
[52] U.S. Cl. ....................................... 422/61; 422/58; 422/102; 436/808; 436/810; 435/810
[58] Field of Search ............... 436/530, 531, 808, 810; 435/810, 295; 422/58, 61, 102

[56] References Cited

U.S. PATENT DOCUMENTS

| | | | |
|---|---|---|---|
| Re. 30,267 | 5/1980 | Bruchi | 23/230 |
| 3,552,925 | 7/1967 | Fetter | 23/230 |
| 3,645,687 | 2/1972 | Nerenberg | 23/230 |
| 3,811,840 | 5/1974 | Bauer et al. | 23/253 |
| 3,849,256 | 11/1974 | Linder | 195/139 |
| 3,888,629 | 6/1975 | Bagshawe | 23/230 |
| 4,246,339 | 1/1981 | Cole et al. | 435/7 |
| 4,270,920 | 6/1981 | Kondo et al. | 23/230 |
| 4,340,479 | 7/1982 | Pall | 210/490 |
| 4,366,241 | 12/1982 | Tom et al. | 435/7 |
| 4,407,943 | 10/1983 | Cole et al. | 435/7 |
| 4,424,279 | 1/1984 | Bohn | 422/61 X |
| 4,427,769 | 1/1984 | Adlercreutz et al. | 422/61 |
| 4,549,655 | 10/1985 | Forsythe et al. | 206/569 |
| 4,559,949 | 12/1985 | Levine | 422/61 |
| 4,623,461 | 11/1986 | Hossom et al. | 210/445 |
| 4,632,901 | 12/1986 | Valkirs et al. | 435/5 |
| 4,645,743 | 2/1987 | Baker et al. | 422/61 |
| 4,717,656 | 1/1988 | Swanljung | 422/58 X |
| 4,727,019 | 2/1988 | Valkirs et al. | 435/5 |
| 4,746,614 | 5/1988 | Devaney | 435/295 |
| 4,770,853 | 9/1988 | Bernstein | 422/58 |
| 4,789,639 | 12/1988 | Fleming | 436/810 |

FOREIGN PATENT DOCUMENTS

PCT/US85/-
00870 5/1985 PCT Int'l Appl. .

Primary Examiner—Robert J. Warden
Assistant Examiner—Lyle Alfandory-Alexander
Attorney, Agent, or Firm—Staas & Halsey

[57] ABSTRACT

A disposable, pre-packaged device is particularly suitable for conducting diagnostic procedures based on immunological reactions using specimens gathered in the absorbent tip of a swab. The device is made up of an elongated holder member which includes structure for supporting and positioning a swab, another holder member hingedly mounted at one end of the swab holder member and which carries a capture media element assemblage suitable for conducting an immunoassay test. The device also includes a cover member hingedly mounted on the opposite end of the swab holder member. The cover member includes structure positioned for pressing the swab tip against the capture element when the device is operated. Thus, the light in the swab tip is squeezed and the test fluid is expressed therefrom and brought into intimate contact with the capture element. The results of the test are visually observable by simply swinging the member which carries the capture element away from the swab holder member.

6 Claims, 2 Drawing Sheets

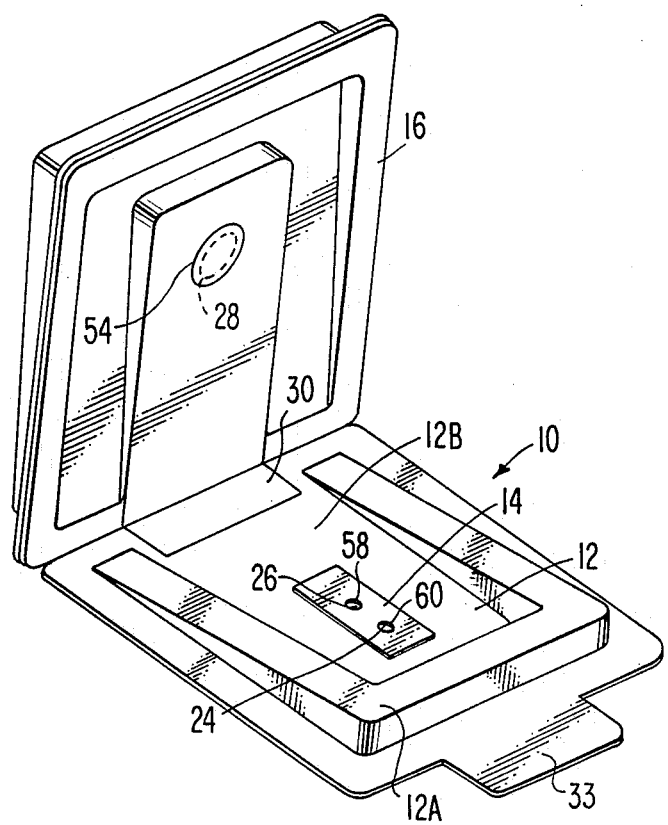
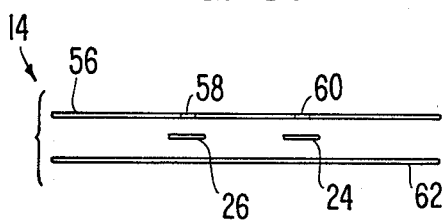
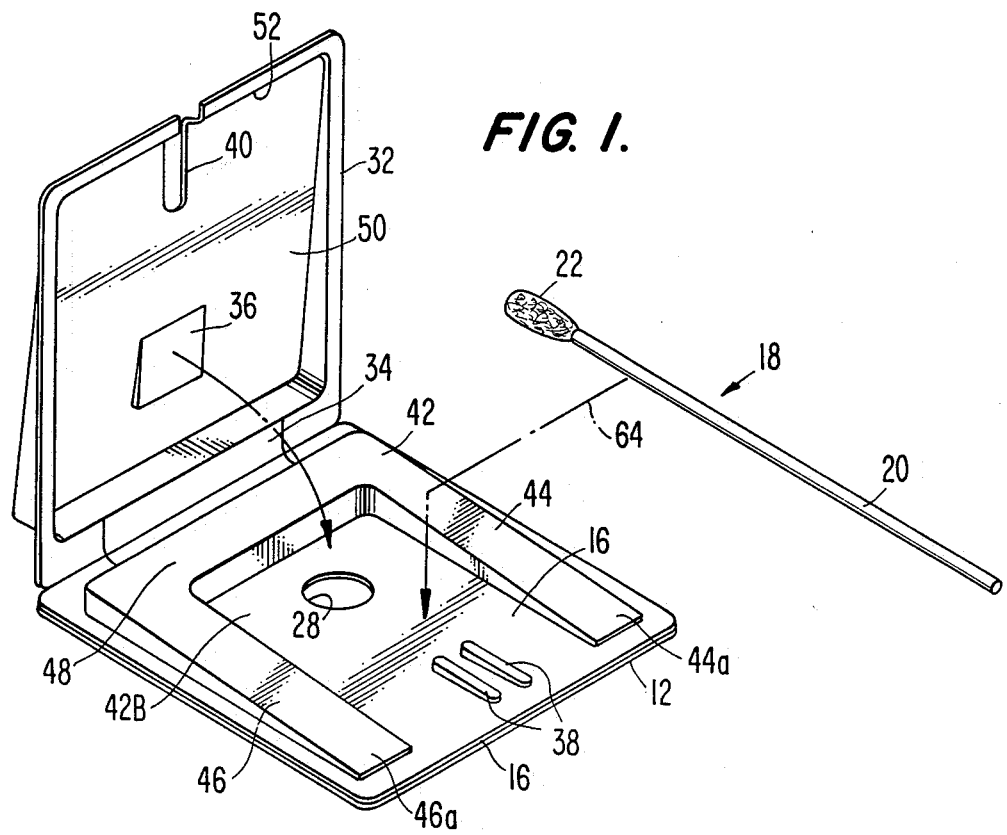

SWAB EXPRESSOR IMMUNOASSAY DEVICE

BACKGROUND OF THE INVENTION

1. Field of the Invention

The present invention relates to devices for conducting immunoassay procedures. More particularly, the invention relates to disposable, pre-packaged devices which are particularly suitable for conducting diagnostic procedures based on immunological reactions using specimens gathered on swabs at remote sites such as physician's offices and homes of users.

2. Description of the Prior Art

Since the important discovery of Milstein and Kohler reported in *Nature* 256: 495-497, 1975, the development of highly sensitive and specific immunoassay procedures has proceeded at a rapid pace. In fields such as clinical medicine, forensic sciences, environmental quality testing, food quality assurance, drug testing and other related areas, it has become possible to determine the presence and/or amount of trace substances in test samples even when such substances are present in very low concentrations in the order of parts per million, or even less. The development of non-radioactive labels or markers, such as enzyme color formers, has facilitated the use of immunoassay diagnostic procedures outside of laboratory settings and in remote sites such as physician's offices and even the homes of the users. In the physician's office, immunological procedures are useful for providing rapid, simple assays which may be performed while the patient is still in the office so that the diagnosis can be accomplished without delay and treatment instituted during a single visit. Without such simple assays, it has often been necessary for the physician to collect a sample from a patient during a first visit and to have the sample analyzed by a clinical laboratory with the results reported back to the physician by the laboratory at a later time. In the meanwhile, the patient was sent home and was required to return for a second visit with the physician in order to receive appropriate treatment and/or medication. Manifestly, such delay was inefficient and inappropriate and in some cases could even be life threatening.

Home testing has become desirable to facilitate testing by the consumer in the privacy of his or her own home. The results of such testing might, for example, indicate the necessity or lack of necessity of a visit to the physician. Examples of useful tests for the "at home" market include tests for pregnancy, ovulation, streptococcus infection and other infections which are detectable by analysis of body fluids such as urine, saliva, throat fluids, pus, vaginal fluids, blood or other appropriate test samples.

For remote site testing, assuming appropriate sensitivity and specificity can be achieved, there are at least three other requirements for practical assay procedures. The first of these desirable factors is speed in that the assay must be performed in an acceptably short period of time, the shorter the better. Stability is also a desirable feature in that the components of the assay should be stable for an extended period of time without refrigeration or special handling. Finally, from a commercial view point it is desirable that the test be convenient to use and as simple as possible requiring only minimal or no instrumentation and precluding mistakes and poor performance resulting in incorrect interpretations.

One of the difficulties encountered in the development of test devices for remote site testing is the provision of a practical pre-packaged disposed device to facilitate efficient, relatively inexpensive, foolproof test procedures. This, of course, requires a device which is inexpensive to construct, which has a shelf life appropriate to the commercial use of the device, which is protected against contamination during handling, which may be simply and conveniently utilized when the appropriate time arises, and which may conveniently and safely be used by even untrained persons.

The device illustrated in U.S. Pat. No. 4,632,901 addresses some of these problems and is available commercially; however, the device has a number of deficiencies including the fact that it is useful only in connection with urine or other pourable fluid samples. Another device for testing pourable fluid samples is illustrated in the co-pending, commonly owned application of Lennon and Murphy, U.S. patent application Ser. No. 107,240, filed Oct. 13, 1987.

Other prior single test devices are illustrated in United States Letters Patent Nos. 4,366,241 and 4,623,461. However, these devices are of limited application and have excessive complexity.

None of these prior art devices addresses the particularly difficult set of problems that are encountered when a sample is collected on a swab or the like for delivery to the test device, such as is necessary in the case of a strep throat test, for example. Rather, to use prior devices with a test sample collected on a swab, it was generally necessary to utilize techniques involving manual expression of the specimen fluid from the swab to form a pourable liquid test mixture or the streaking of the swab on an agar plate.

SUMMARY OF THE INVENTION

The present invention provides relief from many of the shortcomings of the prior devices described above. In this regard, the invention provides a simplified, pre-packaged, disposable test device wherein a sample on the swab is brought directly into intimate contact with a porous capture media means where products of the procedure are captured and may be displayed.

In accordance with the present invention, a disposable, pre-packaged device is provided for conducting an immunoassay procedure. The device is particularly useful in connection with immunoassay procedures wherein a test fluid containing a collectible immunocomposite resulting from an immunoreaction or an immunoreactive component is initially gathered in an absorbent mass such as the absorbent tip of a swab device, then the absorbent mass with the gathered immunocomposite or immunoreactive component containing liquid therein is pressed toward a surface of a porous capture element and the absorbent mass is thus squeezed to thereby cause expression of the fluid containing the immunocomposite or immunoreactive component and the bringing of the expressed fluid into intimate contact with the capture element.

More broadly, the device may be used for conducting an immunoassay procedure wherein a fluid which may contain an immunoreactive analyte to be tested for is initially gathered in an absorbent mass and the fluid and analyte are then caused to be brought into contact with a test element in the conduct of the test.

The device comprises a first holder member including structure for supporting and positioning a capture or test element, a second holder member mountable on the first member and including structure for supporting and positioning a fluid containing absorbent mass such as the tip of a swab in a position adjacent the capture or test element, and a cover member that is mountable on the second holder member and which includes structure positioned for squeezing the absorbent mass containing the test fluid and pressing the mass toward the capture or test element to thereby express the fluid and causing the latter to contact the element when said second holder member is mounted on the first holder member and carries an adsorbent mass and the cover member is mounted on the second member.

BRIEF DESCRIPTION OF THE DRAWINGS

FIG. 1 is an isometric view of a disposable, pre-packaged device embodying the principles and concepts of the present invention and illustrating the constructional details of and the operational relationships between a cover member and a swab positioning holder member;

FIG. 2 is an isometric view of the device illustrating the constructional details of and the operating relationships between the swab holder member and a capture element holder member;

FIG. 3 is an enlarged, exploded view illustrating the structural and operational details of the capture elements and related components.

DETAILED DESCRIPTION OF THE INVENTION

Figure 5:
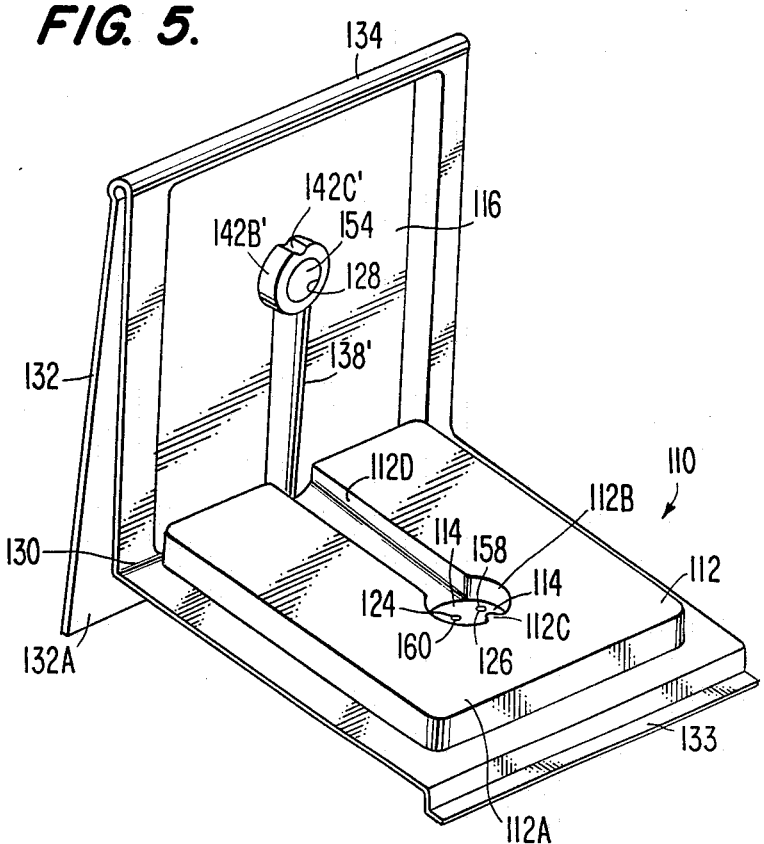
FIGS. 4 and 5 are isometric views similar to FIGURES 1 and 2 respectively, and illustrating a second embodiment of the invention.

The concepts and principles of the present invention are embodied in a disposable, pre-packaged device 10 which is useful for conducting an immunoassay procedure wherein a test fluid is originally gathered in an absorbent mass such as the tip of a swab. The exact type of procedure or protocol utilized is not important for purposes of the present invention other than that the device may be used to facilitate any sort of procedure which results in the production of a collectible or filterable phase that incorporates a tag of some sort to indicate a positive or negative test result. Generally speaking, the device 10 of the present invention may be utilized in connection with procedures which employ a visually detectable colored or color forming tag such as an enzyme or metal sol particle tag to indicate the occurrence or non-occurrence of a specific immunoreaction. However, it is within the perceived usefulness of the invention that the device might well be employed in connection with procedures wherein a reactant is tagged with an instrument detectable tag such as a radioactive isotope, a fluorescent material or a chemiluminescent material.

Immunoassay kits employing enzyme markers are presently commercially available for determining such conditions as pregnancy and ovulation in the physician's office and in the home of the user. Such kits are described in said '901 patent and in said co-pending application Ser. No. 107,240. In the '901 patent and in some of the procedures of the 240 application, an enzyme labelled antibody reacts with an antigen to form an immunocomposite that is collected on a porous membrane upon further reaction of the antigen with antibody immobilized on the porous capture membrane. The enzyme tag enters into a reaction system with chemicals fixed on the membrane to produce a visible color.

In the co-pending application of Cole, Davis and Sigillo, entitled "Metal Sol Capture Immunoassay Procedure, Kit For Use Therein and Captured Metal Containing Composite", Ser. No. 105,285, filed Oct. 7, 1987, which application is also assigned to the assignee of the present application, a metal particle label is utilized as the label and a collectible, solid phase, metal containing composite is formed. The composite may be collected by filtration on a filter element or the like where the presence of analyte in the original sample is determined or detected by evaluating, through direct visual examination, the presence of metal in the collected solid phase.

The entireties of the disclosures of said co-pending applications Ser. Nos. 105,285 and 107,240 are hereby specifically incorporated herein by reference.

The device 10, in its preferred form, comprises a first holder member or tray 12 for supporting a capture media element assemblage 14 in a position for conduct of an assay procedure. The device 10 also comprises a second holder member or tray 16 for supporting and positioning a swab 18 comprising a stick 20 and an absorbent or porous mass or tip 22, with the latter in a position adjacent the capture elements 24 and 26 which form a part of the assemblage 14. In this connection, and with particular reference to FIG. 1, tray 16 includes structure in the form of parallel guides 38 for maintaining swab 18 in a position where the swab tip 22 is disposed adjacent elements 24 and 26 via an access opening 28 provided in the floor of tray 16.

As can be seen viewing FIG. 2, tray 16 is attached to tray 12 by a flexible hinge 30 which facilitates mounting of tray 16 on tray 12 during the conduct of assay procedures and the opening of the device into the FIG. 2 position so that the capture elements 24 and 26 may readily be visualized upon completion of the test procedures. Trays 16 and 12 are illustrated in their closed positions with tray 16 mounted in its operational position atop tray 12 in FIG. 1 wherein the entire device has been rotated 180° in the horizontal plane relative to the FIG. 2 position so that the tab 33 of tray 12 is located behind the device and is thus hidden from view in FIG. 1.

With reference to FIG. 1, the device 10 also includes a cover member 32. Cover member 32 is attached to tray 16 by another flexible hinge 34 facilitating movement of cover member 32 relative to tray 16 about the axis provided by hinge 34, as can be seen viewing FIG. 1. Cover member 32 includes structure in the form of an abutment 36 positioned for squeezing tip 22 toward capture elements 24 and 26 when cover member 32 swings about the axis of hinge 34 and into its closed and mounted position relative to tray 16. As can be seen viewing FIG. 1, tray 16 is provided with the pair of parallel guides 38, and swab 18 is inserted therein by placing tip 22 as close as possible to the center of access opening 28 and then moving stick 20 downwardly for insertion between guide members 38. Cover member 32 has an elongated slot 40 which provides clearance for stick 20 to allow cover member 32 to be closed, an brought into its closed mounted operating position relative to tray 16.

Tray 16 is provided with a U-shaped dam 42 which essentially encompasses swab tip 22 when the swab 18 is positioned in its operational disposition. In the preferred form of the invention the opposed arms 44 and 46 of dam 42 are tapered downwardly so that the height of dam 42 is less at the distal ends 44A and 46A of arms 44 and 46 than it is at the arm connecting bight portion 48 of dam 42. Cover member 32 is provided with a correspondingly shaped and mating indentation 50 which mates with and surrounds dam 42 when the cover member 42 and tray 16 are in their closed dispositions. Indentation 50 also presents an end wall 5 which cooperates with distal ends 44A and 46A of dam 42 when cover member 32 is in its closed position so that the space in the proximity of tip 22 is completely surrounded by the device when cover member 32 is in its closed position. That is to say, tip 22 is confined within the well 42B bounded by dam 42 and cover 32 when the latter is mounted in its operating position on tray 16, and the only manner in which fluid is able to leave well 42B is through access opening 28.

As can be seen viewing FIG. 2, tray 12 is provided with a dam 12A which serves essentially the same purpose as dam 42 by preventing test fluid from escaping from the well 12B that surrounds assemblage 14 during operation.

A filter member 54 may be disposed in covering relationship relative to access opening 28 as can best be seen in FIG. 2. And when tray 16 is mounted in its operating disposition on top of tray 12, filter element 54 is disposed in covering and essentially directly contacting relationship relative to capture elements 24 and 26.

The capture media element assemblage 14 is illustrated in exploded view in FIG. 3 where it can be seen that assemblage 14 comprises a flow director 56 having holes 58 and 60 therein, capture elements 24 and 26 and an absorbent pad 62.

Tray members 12 and 16 and cover member 32 may be constructed of plastic or glass or any other suitably inert material, and these components may preferably be made by thermal forming from thin sheets of a thermoplastic material such as polystyrene. The only real limitation on the materials of construction for device 10 being that the same must be inert to the reactants and reaction products.

Hinges 34 and 30 may preferably be constructed of an adhesive backed plastic strip (adhesive tape) which is thin enough to provide the necessary flexibility and yet strong enough to permit handling and operation in accordance with the desired operational sequences. Such materials are well known.

Absorbent pad 62 may be constructed of an absorbent material having capillary passages extending therethrough in a diversity of directions which are both transverse to and generally parallel to the surfaces of pad 62. There are a number of materials which are well known to those of skill in the art to which the present invention pertains that may be used to construct absorbent pad 62. Such materials include hydrophilic polymers, particulate adsorbents, glass fibers, cotton fibers, cellulose fibers, wood pulp and/or sponge. Other materials which may find use as pad 62 include polysaccharides, for example cellulosic materials, such as paper and cellulose acetate. Cellulose acetate fibers arranged in the same manner as in a cigarette filter may be utilized to construct absorbent pad 62. Another useful material is the absorbent material used in a tampon. A particularly useful material for construction of pad 62 is a cellulosic pad material, approximately 0.036" thick, available commercially from Schleicher and Schuell. In any event, the important features of the materials useful in the construction of pad 62 are simply that the same be capable of absorbing a substantial quantity of fluid materials and that the same possess sufficient structural integrity to facilitate the initial construction of the assemblage 14. Further useful absorbent materials are disclosed, for example, in U.S. Letters Pat. Nos. 4,246,339; 4,623,461; 4,632,901 and 4,366,241.

The porous capture media elements 24 and 26 may take any one of several different forms depending on the type of immunoassay procedure which is utilized. For example, if the immunoassay involves an immobilized antibody ELISA technique, elements 24 and 26 may be membranes having a coreactant antibody for the reagent to be assayed in the test liquid sample immobilized on the internal and external surfaces thereof. Such membranes are utilized in the procedures disclosed in U.S. Letters Pat. No. 4,246,339 and in International PCT Publication No. WO85/05451 (International Application No. PCT/US85/00870). Membranes useful in connection with such procedures are fully disclosed and described in U.S. Letters Patent No. 4,340,479. Manifestly, methods for binding immunoreactants to such membranes are well known to those skilled in the art. Elements 24 and 26 are preferably about 0.006" thick and the same may be constructed from a nylon membrane material available commercially under the tradename "Gelman Ultrabind."

In another form of the invention, porous capture media elements 24 and 26 may be composed of such things as glass fiber filters (Whatman GF/A), regenerated cellulosic membranes (Schleicher and Schuell) and microporous membranes (Millipore MF series membranes HAWP, SSWP, SMWP and SCWP with pore sizes of 0.45, 3, 5 and 8 microns respectively). All of these materials have been successfully utilized for capturing and collecting a solid phase product resulting from an immunoassay procedure. In particular such materials have been found to be useful for capturing the collectible, solid phase, metal containing composites which result from the immunoassay procedures described in said co-pending and co-assigned '285 application of Cole et al. Manifestly, in such process the porous capture media element simply comprises a filter element having pores of a size to prevent passage of the reaCtion products to be captured and collected. Accordingly, the desired reaction products accumulate on the surface of the element and are available there for visual inspection.

Flow director 56 may preferably be constructed of a non-adsorptive polyester film such as Mylar. Flow director 56 may preferably be approximately 2 mm in thickness. The flow directing holes 58 and 60 should be positioned so as to directly overly collector elements 24 and 26 and the latter should simply be large enough so that all of the liquid flowing through holes 58 and 60 is directed appropriately through the pores of the elements 24 and 26.

The capture media element assemblage 14 is illustrated in an exploded condition in FIG. 3, and to facilitate assembly thereof, the back side of director 56 may be coated with an acrylic adhesive, for example, so as to hold the elements 24 and 26 in place and to hold the flow director 56 tightly against the absorbent pad 62 so that the assemblage 14 may be readily manipulated and handled as a single component. Manifestly, an adhesive material may be applied to the back of absorbent layer 62 so as to adhere assemblage 14 to tray 12 in the desired location as illustrated in FIG. 2. Alternatively, pieces of tape or a single piece of tape with openings therein at the location at holes 58 and 60 might be used to hold structure 14 in place on tray 16.

Filter 54 may preferably be a microporous nylon membrane having a porosity in the order of approximately 0.5 microns. Such membranes are commercially available. A preferred membrane for use in the construction of filter 54 is available under the trade name "Pall LoProdyne". In the preferred form of the invention, the nylon membrane utilized to form the filter 54 should be approximately 0.006" thick and the same may be held in place on the under surface of tray 16, as illustrated in FIG. 2, using an adhesive. Filter 54 serves to remove debris present in the test fluid and which might interfere with the operation of the test materials and procedures and is located on the underside of tray 16 to facilitate movement to an out-of-the-way-position when the device is opened so that the test results may be read.

In the operation of device 10, a specimen is collected on the absorbent tip 22 of swab 18. For example, in conducting a test for strep throat, a swab is utilized to swab the tonsil area. The swab may then be contacted with appropriate immunoreagents in a liquid system and the mixture may then be allowed to incubate for a period of time, all as is well known to those skilled in the immunoassay art. After a sufficient incubation period, during which the swab tip may remain in contact with the liquid system containing other immunoreagents, the reaction mixture, or at least a portion thereof, will have been gathered up in and absorbed by the absorbent tip 22.

In the form of the invention wherein an antibody is immobilized on one or the other or both of elements 24 and 26, the reaction fluid in the swab tip may simply contain unreacted test analyte to be determined or a reactive immunocomposite comprising a labelled antibody bound to the test analyte. On the other hand, in the form of the invention which might utilize the gold sol capture immunoassay procedure described in said '285 application of Cole et al., the reaction fluid in the swab tip may contain an immunocomposite comprising a completed sandwich consisting of a labelled antibody, the test analyte and a second antibody bound to a solid particle too large to traverse the pores of the capture elements 24 and 26.

The swab which has gathered and absorbed the liquid reaction mixture is then placed in device 10 as indicated by the arrow 64 in FIG. 1. After the initial placement of swab 18, the absorbent tip 22 which contains the absorbed reaction liquid will be disposed essentially centrally of access opening 28 and the stick 20 will be positioned so as to extend between guide members 38. The trays 16 and 12 will have previously been closed so that filter 54 is in direct and immediate contact with flow director 56. Upon movement of cover 32 into its closed position in mounted relationship relative to tray 16, abutment 36 contacts absorbent tip 22 to squeeze and deform the latter and express the reaction mixture therefrom and force the absorbent tip 22 into intimate contact with filter 54. In this condition the absorbent tip 22 is essentially in direct capillary communication with the elements 24 and 26 of capture media element assemblage structure 14 and thus the liquid expressed from absorbent tip 22 by the pressure exerted by abutment 36 is channeled through filter 54 and then through elements 24 and 26. The movement of the liquid through elements 24 and 26 is enhanced by the action of pad 62 which, because of its absorbent structure and nature, sucks up the liquid and pulls it through the elements 24 and 26.

As is known to those of skill in the art to which the present invention pertains, elements 24 and 26 may consist of nylon membranes to which different antibodies, each specific to a different antigen, have been immobilized. Thus, the device might be utilized to test for two totally different conditions. Moreover, as is understood by those of skill in the art, one of the elements 24, 26 might be utilized to test for a condition and the other might be utilized as a control. Furthermore, there is no limitation as to the number of elements 24, 26 to be placed beneath access opening 28 other than the physical size of the device and other such physical constraints. Thus, the device of the invention might include means for testing for a multiplicity of conditions, each causing respective analytes to be present in the same specimen. Moreover, a given test procedure might require a multiplicity of controls, each requiring a respective element 24 or 26 disposed beneath a corresponding flow director hole.

Generally speaking, as is well known to those skilled in the art to which the present invention pertains, and as has been fully explained in the disclosures of the '901 patent and the '285 and '240 co-pending applications identified above, formation of coloration on the surface of elements 24 and/or 26 provides an almost instantaneous indication of the results of the assay, whether the same involves a metal sol tag in accordance with the procedure disclosed in the '285 Cole et al. application, or an enzyme tag and an immobilized antibody, such as is disclosed in U.S. Letters Patent No. 4,407,943. Such instantaneous coloration can be observed simply by separating trays 12 and 16 utilizing the tab 33. Thus, when the device 10 is opened up into the position illustrated in FIG. 2, the color indicating a positive or negative result will appear through hole 60 and/or 58. It is important to note in this respect that the filter 54 is preferably carried by the tray 16 so that it and the debris thereon are moved out of the way when the device is opened to read the results of the test. Thus, the filter does not need to be handled individually. Moreover, when the device is opened to read the results, the swab remains encased by top member 32 and tray 16 and thus the device and the swab may subsequently be discarded without the need for handling the swab separately.

Figure 4:
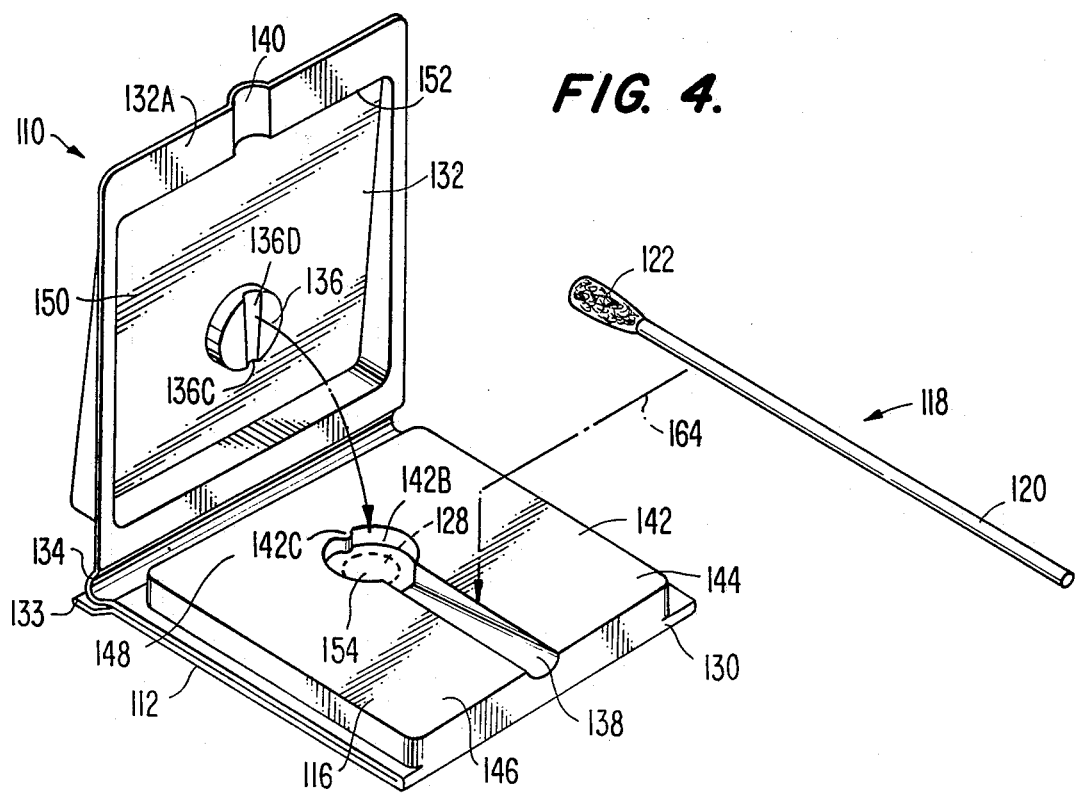

Another embodiment of the device of the invention is illustrated in FIGS. 4 and 5 and is there designated by the reference numeral 110. Parts illustrated in FIGS. 4 and 5 which correspond generally with the parts of FIGS. 1 and 2 are designated by similar reference numerals except that the reference numerals in FIGS. 4 and 5 are in the 100's. Thus, the tray 112 of FIGS. 4 and 5 corresponds with the tray 12 of FIGS. 2 and 3, the assemblage 114 of FIGS. 4 and 5 corresponds with the assemblage 14 of FIGS. 1 and 2 and so on.

In essence the device 110 of FIGS. 4 and 5 corresponds in both structure and function with the device 10 of FIGS. 1 and 2. However, a number of structural modifications have been incorporated to facilitate manufacture and/or operation. These modifications are discussed hereinbelow. Features which are not discussed here may be understood as being essentially identical in structure and function to the device 10 as described above.

As can be seen viewing FIGS. 4 and 5, the device 110 may be constructed of a single piece of thermoformed plastic and the hinges 130 and 134 are provided by lines of weakness or flexibility resulting from the configuration of the molding die. Additionally, cover 132 is provided with a lip 132A to facilitate manipulation of the device during use.

With specific reference to FIG. 5, tray 112 is provided with a dam structure 112A which closely surrounds the well 112B where the assemblage 114 is located. Well 112B is generally circular in form except for a small projection 112C which protrudes into the otherwise circular well 112B and extends vertically from the top to the bottom of the well. Assemblage 114 may preferably be shaped to correspond with the interior shape of the well 112B; however, the assemblage 114 is otherwise substantially the same in structure, components and function as assemblage 14 of device 10. An elongated groove 112D extends from well 112B toward hinge 130, as can be seen, so as to provide clearance to accommodate other components and structural elements of device 110 when trays 116 and 112 are closed to facilitate operation of the device.

With reference to FIG. 4, the dam 142 is designed to closely confine the tip 122 of swab 118. Thus, dam 142 presents a well 142B which is essentially circular. A groove 138 is provided for receiving and guiding the stick 120 of the swab 118. And the filter 154, which serves the same purpose as the filter 54 of device 10 and may be constructed of the same materials, is located in the bottom of well 142B. Thus, the filter 154 preferably has a shape which conforms to the internal shape of well 142B. With reference to FIG. 5, the respective under surfaces 142B' and 138' of well 142B and guide groove 138 can be seen. This is the result of the device 110 having been formed by thermoforming from a single sheet of plastic material. The configurations of surfaces 142B'and 138' are thus conformed to complimentarily nest in groove 112D and well 112B respectively when the device is closed and tray 116 is mounted on tray 112. Additionally, a projection 142C is provided in well 142B, and as can best be seen in FIG. 4, the under surface 142B'of well 142B presents a notch 142C' that essentially is shaped complimentarily relative to projection 112C. Projection 112C and notch 142C' thus are complimentarily mated for guiding trays 112 and 116 into proper alignment when the latter are nested for operation.

With further reference to FIG. 4, abutment 136 is essentially of circular configuration and the same is complimentarily configured so as to be received within well 142B. Thus, abutment 136 is provided with a notch 136C which is complimentarily configured to receive projection 142C when the device is closed. Additionally, a transverse groove 136D is provided across the top of abutment 136 to assist in the squeezing of tip 122 during the use of the device 110. A groove 140 is provided in lip 132A to accommodate stick 120 when the device is closed and cover member 132 is mounted on tray 116.

It will be readily apparent to those of ordinary skill in the art, that while the device in the present invention has been described in connection with certain specific immunoassay procedures, the same might also be utilized in connection with other immunoassay procedures that involve a liquid phase reaction and production of a labelled immunoreaction product that is capturable on a porous media capture element, either by a filtration process or an immunochemical reaction. In this regard, capture elements 24 and 26 may be filter elements having pores of a size to prevent passage of a desired collectible reaction product, or a porous element, such as a microporous membrane, to which is bound an immunoreactive substance that is specifically reactive in the desired immunoassay

We claim:
1. A disposable, pre-packaged device for conducting an immunoassay procedure to detect an immunoreactive test analyte wherein a fluid material containing an immunoreactive test analyte or an immunocomposite formed from such a test analyte is initially gathered in an absorbent mass, the absorbent mass with said fluid material therein is pressed toward a surface of a porous capture element capable of collecting the test analyte or said immunocomposite and the absorbent mass is thus squeezed to thereby express said fluid material and bring the expressed fluid material and its contents into intimate contact with the capture element where the test analyte or immunocomposite formed therefrom are collected and the test analyte detected to indicate a positive result, said device comprising:
   a first holder member including structure for supporting and positioning a said capture element;
   a second holder member hingedly mounted on said first holder member and including structure for supporting and positioning an absorbent mass containing said fluid material in a position adjacent the capture element; and
   a cover member hingedly mounted on said second holder member, said cover member including abutment structure configured and positioned to protrude toward the absorbent mass and contact abutment structure and the second holder member and press the mass against the capture element to thereby express fluid from the absorbent mass and cause the expressed fluid and its contents to come into contact with the capture element when said second holder member is mounted on the first holder member and the cover member is mounted on the second holder member.

2. A device as set forth in claim 1, wherein said second holder member is elongated, said cover member is hingedly mounted at one end of the second holder member and said first holder member is hingedly mounted at the other end of the second holder member.

3. The device as set forth in claim 1, wherein said second holder member and said cover member are removable from the first holder member as a unit and with the absorbent mass enclosed therein.

4. The device as set forth in clam 1, wherein said second holder member and said cover member include structure for surrounding and confining the absorbent mass and the fluid expressed therefrom when the mass is squeezed, said second holder member and said cover member being removable from the first holder member as a unit and with the absorbent mass enclosed therein to facilitate viewing of the capture element and disposal of the absorbent mass at the completion of the immunoassay procedure.

5. The device as set forth in claim 1, wherein an access hole is provided in said second holder member in a position to facilitate direct fluid communication between said absorbent mass and the capture element when the mass is squeezed.

6. The device as set forth in claim 5, wherein is provided a filter element carried by said second holder member in covering relationship to said access hole.

* * * * *